Figure 1:
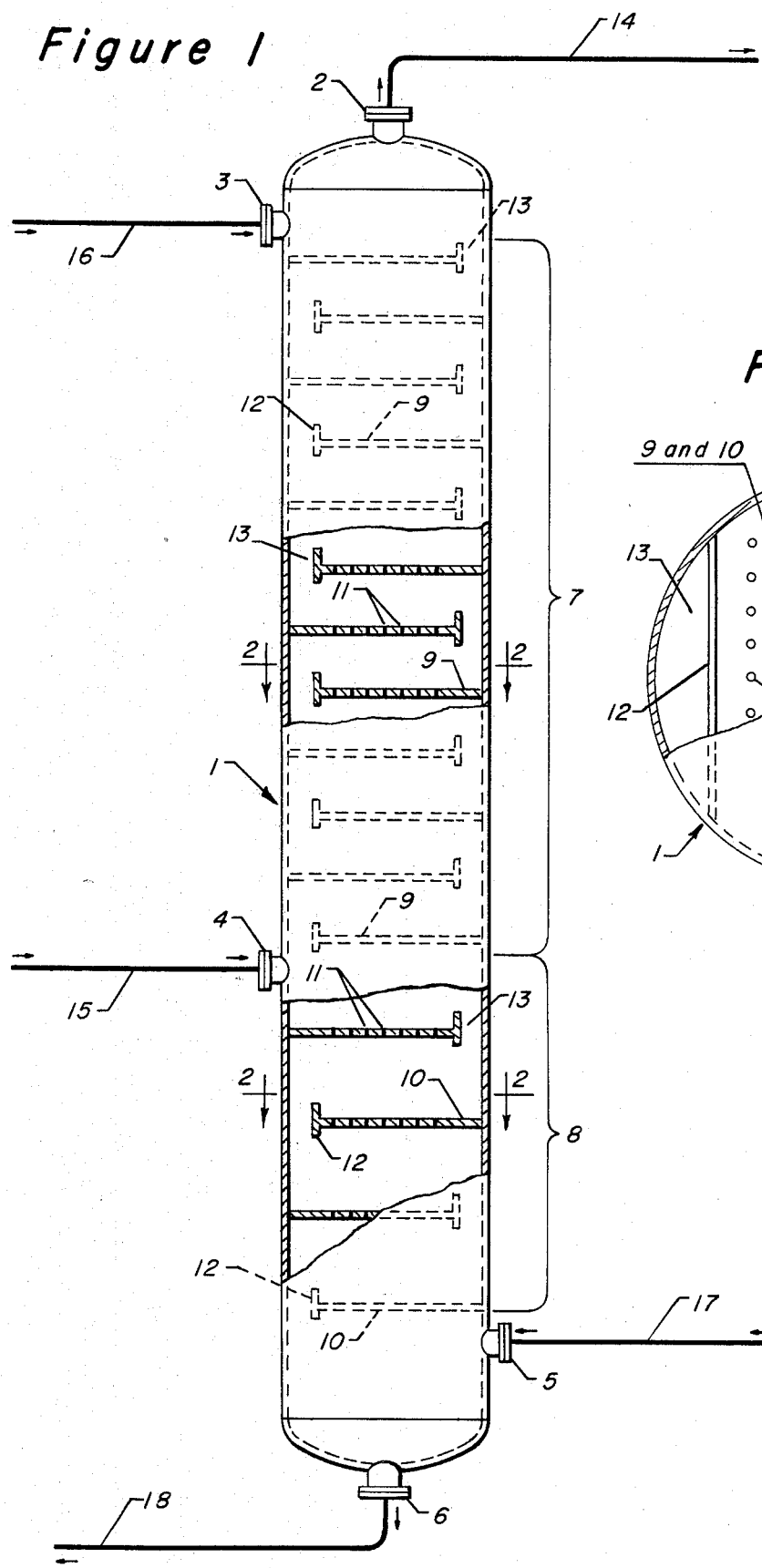

United States Patent [19]

Winter, III

[11] 4,336,106

[45] * Jun. 22, 1982

[54] APPARATUS FOR THE SOLVENT EXTRACTION OF AROMATIC HYDROCARBONS FROM A HYDROCARBON MIXTURE

[75] Inventor: George R. Winter, III, Mt. Prospect, Ill.

[73] Assignee: UOP Inc., Des Plaines, Ill.

[*] Notice: The portion of the term of this patent subsequent to Oct. 6, 1998, has been disclaimed.

[21] Appl. No.: 198,037

[22] Filed: Oct. 17, 1980

[51] Int. Cl.³ .................. B01D 11/04; C10C 3/08
[52] U.S. Cl. .................. 196/14.52; 202/158; 210/511; 422/256
[58] Field of Search .................. 196/14.52; 208/317, 208/318; 260/705; 422/275, 256, 257, 259; 202/158; 203/91; 261/113; 210/511, 634

[56] References Cited

U.S. PATENT DOCUMENTS

| | | | |
|---|---|---|---|
| 2,139,871 | 12/1938 | Wilson et al. | 196/14.52 |
| 3,143,482 | 8/1964 | MeLeod et al. | 202/158 |
| 3,361,664 | 1/1968 | Broughton et al. | 208/321 |
| 3,433,735 | 3/1969 | Broughton | 208/325 |
| 3,979,281 | 9/1976 | Gerhold | 260/705 |
| 4,039,389 | 8/1977 | Christman | 196/14.52 |

OTHER PUBLICATIONS

Kirk-Otmer; vol. 9; pp. 691-693; 1978.

Primary Examiner—Bradley Garris
Attorney, Agent, or Firm—James R. Hoatson, Jr.; Robert W. Welch; William H. Page, II

[57] ABSTRACT

A multiple stage extractor column for the countercurrent contact of an upwardly moving hydrocarbon phase and a downwardly moving solvent phase is disclosed. The column is particularly useful for the solvent extraction of aromatics from a hydrocarbon feedstock containing $C_9$ aromatics. The contactor column embodies an upper extraction section comprising a first plurality of perforated extraction trays and a backwash section comprising a second plurality of perforated extraction trays, said second plurality of trays being vertically spaced apart a greater distance than the trays of said first plurality whereby the solvent/hydrocarbon interface at the bottom of the column is more readily controlled.

4 Claims, 2 Drawing Figures

APPARATUS FOR THE SOLVENT EXTRACTION OF AROMATIC HYDROCARBONS FROM A HYDROCARBON MIXTURE

This invention relates to the solvent extraction of aromatic hydrocarbons from a mixed hydrocarbon feedstock. In particular, this invention relates to the solvent extraction of aromatic hydrocarbons from a mixed hydrocarbon feedstock whereby substantially complete separation is effected in two stages, namely, a solvent extraction stage and an extractive stripping stage.

It is generally recognized that the lighter non-aromatic hydrocarbons of a mixed hydrocarbon feedstock are more soluble in the aromatics-selective solvent than are the heavier non-aromatics and consequently less readily separated in the solvent extraction stage than are the heavier non-aromatics. On the other hand, the lighter non-aromatic hydrocarbons are more readily stripped from said solvent by extractive stripping than are the heavier non-aromatics. Thus, it is the practice to treat the hydrocarbon feedstock in an extractor column in contact with a lean aromatics-selective solvent at conditions to produce an overhead raffinate steam comprising non-aromatic hydrocarbons, and a bottoms aromatic-rich solvent stream comprising some of the lighter non-aromatics. The lighter non-aromatics are then stripped from the aromatic-rich solvent, along with some of the lighter aromatics, in an extractive stripper column to produce a high purity aromatic extract. The lighter non-aromatic hydrocarbons are generally recycled to a backwash section of the extractor column as reflux. The aromatic extraction process is more clearly set forth in U.S. Pat. Nos. 3,433,735 and 3,361,664 wherein the solvent is sulfolane admixed with water. These patents and other published literature describe typical processing steps and operating conditions for the extractor column to produce a non-aromatic hydrocarbon raffinate and an aromatic-rich solvent, and for the subsequent extractive stripper column wherein the lighter non-aromatics are separated from said solvent to provide a high purity aromatic extract.

The extractor column is typically a multiple stage liquid-liquid contactor column comprising an overhead outlet means for the hydrocarbon raffinate, an upper inlet means for the lean solvent, an intermediate inlet means for the hydrocarbon feedstock, a lower inlet means for the hydrocarbon reflux, and a bottom outlet means for the aromatic-rich solvent. The multiple stages of said column are substantially uniform and comprise a plurality of vertically spaced-apart sieve trays or decks designed to retain a layer of the heavier solvent phase thereon while allowing a rain of droplets through the perforations into the stage below. The lighter hydrocarbon phase ascending through the column is passed from stage to stage by way of an upcomer designed to guide the hydrocarbon phase into each stage at a point above the solvent layer contained therein, and then laterally across said stage in contact with the solvent droplets raining down through the sieve tray or deck of the stage above and into the next higher stage.

Those stages lying generally below the hydrocarbon feed inlet are commonly referred to as the backwash section. In the backwash section, the lighter non-aromatics recovered from the extractive stripper column and recycled to said backwash section as reflux, displace the heavier non-aromatics dissolved in the solvent phase—the displaced heavier non-aromatics being then recovered in the overhead hydrocarbon raffinate. The heavier non-aromatic content of the solvent entering the extractive stripper is thus reduced, and an aromatic extract of improved purity results.

The extractor column is operated as a liquid-full vessel, and the descending solvent is allowed to accumulate in the bottom of the column to establish a hydrocarbon/solvent interface. A bottom interface control is provided to assure that no free hydrocarbon phase leaves the bottom of the column to enter and upset the extractive stripper column operation.

This invention is particularly concerned with the loss of interface control which has been experienced when treating a hydrocarbon feedstock containing $C_9$ aromatics in an extractor column having a relatively large backwash section. The loss of said interface control has now been determined to result from a significant increase in the upward velocity of the hydrocarbon phase in the backwash section. Ostensibly, the increased velocity occurs as a result of the displacement of $C_9$ aromatics from the solvent in the backwash section—$C_9$ aromatics being displaced by lighter aromatics, i.e., benzene, contained in the reflux recycled from the extractive stripper column. The displaced aromatics join the hydrocarbon phase to increase its velocity as it moves upwardly through the backwash section of the column. The $C_9$ aromatics are carried upwardly until reabsorbed by the lean solvent in the upper extraction section of the extractor column. The cycle is then repeated until the amount of $C_9$ aromatics escaping with the rich solvent equals the amount of $C_9$ aromatics in the hydrocarbon feedstock. In any case, the resulting increased velocity of the hydrocarbon phase laterally traversing the several backwash stages, impedes the downward progress of the solvent droplets, and at least a portion of said droplets are carried back through the upcomer means to the preceding stage from which they originated. The solvent phase thus becomes stacked up in the backwash section and is precluded from accumulating in the bottom of the column to maintain the desired hydrocarbon/solvent interface.

It is therefore an object of this invention to provide a multiple stage extractor column having a modified backwash section designed to obviate solvent stacking therein under conditions of increased hydrocarbon phase velocities.

Thus, in one of its broad aspects, the present invention embodies a multiple stage extractor column for countercurrent contact of an upwardly moving hydrocarbon phase and a downwardly moving solvent phase which comprises an enclosed vertically elongated shell having an overhead raffinate outlet means, an upper lean solvent inlet means, an intermediate hydrocarbon feedstock inlet means, a lower hydrocarbon reflux inlet means, and a bottom aromatics-rich solvent outlet means; an upper extraction section comprising a first plurality of vertically spaced apart perforated extraction trays, including upcomer means, traversing the interior of said shell in a horizontal plane; a lower backwash section comprising a second plurality of vertically spaced apart perforated extraction trays, including upcomer means, traversing the interior of said shell in a horizontal plane; and the extraction trays of said second plurality being vertically spaced a greater distance than the extraction trays of said first plurality.

By the device of providing a greater spacing between the trays comprising the backwash section of the extractor column, solvent hold-up, resulting from increased hydrocarbon phase velocities, is substantially obviated, and the bottom hydrocarbon/solvent interface is more readily controlled. By providing said greater spacing, the velocity of the hydrocarbon phase horizontally traversing the extraction stages between the trays comprising the backwash section is moderated to the extent that the solvent droplets are allowed to continue their normal gravitational flow.

Other objects and embodiments of this invention will become apparent in the following more detailed specification.

The extractor column herein contemplated is a vertical cylindrical column generally containing from about 60 to about 120 sieve trays. The trays are evenly spaced apart, generally at a distance of from about 0.5' to about 1.5'. The column is adapted for use with a rising liquid hydrocarbon stream which is introduced at an intermediate point in the column and passes upwardly through risers or upcomers in the trays, and with a higher density solvent composition which is introduced into the upper portion of the column and passes downwardly through perforations in the trays. That portion of the column extending above the hydrocarbon feedstock inlet means is referred to herein as the extraction section, and that portion extending below said inlet means is referred to as the backwash section.

The efficiency of a given extractor column, as employed herein, is largely dependent on its ability to effect an optimum dispersion of a selected solvent composition in the hydrocarbon feedstock. An optimum dispersion is in turn partly dependent on the velocity of the hydrocarbon phase traversing each of the several extraction stages, and partly on the design of the perforated extraction trays, including the upcomer means associated therewith. While smaller solvent droplets, as determined by the cross-sectional area of the individual perforations in the trays, will normally effect a greater dispersion of the solvent in the hydrocarbon phase, they will not necessarily effect an optimum dispersion. One of the factors limiting the minimum size of the droplets is their ability to gravitate through an extraction stage without being swept up in the hydrocarbon stream and returned through the upcomer means to the stage from which they originated. Accordingly, the extraction trays have been designed by prior art methods to deliver peak efficiency at the solvent extraction conditions which exist in the extractor column. Typically, the extraction trays will be uniformly spaced apart, and comprise upcomer means uniformly sized, to accommodate a predetermined hydrocarbon throughput at a predetermined hydrocarbon velocity. The extraction trays will further typically comprise uniformly spaced apart perforations having a cross-sectional area designed to effect an optimum dispersion of solvent droplets at said predetermined hydrocarbon velocity.

Pursuant to the present invention, control of the hydrocarbon/solvent interface at the bottom of the extractor column is facilitated by the device of increasing the tray spacing in the backwash section of the extractor column with respect to the tray spacing in the extraction section thereof. Preferably, the tray spacing in the backwash section will be from about $\frac{1}{8}$ to about $\frac{1}{2}$ greater than the spacing between the trays of the extraction section. Thus, where the trays in the extraction section have been uniformly spaced apart a distance of from about 0.5' to about 1.5' to accommodate a predetermined hydrocarbon throughput at a predetermined velocity, the trays in the backwash section will be uniformly spaced apart a greater distance in the range of from about 0.625' to about 2.25'. The present invention is especially useful in the treating of hydrocarbon feedstocks containing $C_9$ aromatic hydrocarbons, and particularly in the treating of hydrocarbon feedstocks containing $C_9$ aromatic hydrocarbons in an extractor column having a relatively large backwash section comprising about the lower one-third of said column.

Aromatics-selective solvents heretofore described as useful to extract aromatic hydrocarbons from a mixture thereof with non-aromatic hydrocarbons, as herein contemplated, generally include nitrobenzene, N-methyl-1-pyrrolidone, and also aliphatic and cyclic alcohols as well as glycol and the ether and ester derivatives thereof. The mono- and polyalkylene glycols, in which the alkylene group contains from 2 to 4 carbon atoms, such as ethylene glycol, diethylene glycol, triethylene glycol, tetraethylene glycol, propylene glycol, dipropylene glycol, tripropylene glycol, and the like, as well as the methyl, ethyl, propyl and butyl ethers, and the acetic acid esters thereof, have been described as a particularly useful class of solvents useful in admixture with water. Various phenols, such as phenol and resorcinol, and their alkyl ethers, such as p-cresol and the like, are also described as effective solvents. Certain aliphatic nitriles, cyano-substituted ethers and amines, and diethers and polyalkylene polyamines have also been suggested as a useful group of solvents. A preferred class of solvents are those commonly referred to as the sulfolane type, sulfolane (tetrahydrothiophene, 1-1, dioxane) being particularly preferred. Sulfolane type solvents further include the various sulfolane derivatives comprising one or more alkyl, alkoxy and/or aralkoxy substitutents generally containing up to about 12 carbon atoms. The sulfolenes, such as 2-sulfolene and 3-sulfolene, are also among the preferred solvents. In any case, solvent selectivity is enhanced by the addition of water. The inclusion of water, although somewhat reducing the solubility of aromatics in the solvent, greatly decreases the solubility of the raffinate components as well as the solubility of the solvent in the raffinate. Generally, the solvent will contain from about 0.5 to about 25 wt.% water, and preferably from about 3 to about 15 wt.% depending on the particular solvent and the process conditions under which it is utilized.

The extractor column is typically operated at an elevated temperature and at an elevated pressure sufficient to maintain the hydrocarbon feedstock, solvent and backwash streams in a liquid phase. Suitable temperatures range from about 25° to about 205° C., and preferably from about 80° to about 150° C. Suitable pressures range from about atmospheric up to about 400 psig., pressures in the 50–150 psig. range being preferred. Generally, the volume of backwash recycled to the backwash section from the extractive stripper column, is at least 10 vol.% of the extract phase leaving the extractor column. The solvent to hydrocarbon feedstock ratio is in the range of from about 1:1 to about 15:1, and preferably in the range of from about 2:1 to about 5:1.

The extractive stripper column is operated at moderate pressures and at a sufficiently high reboiler temperature to drive all of the non-aromatic components and some of the lighter aromatics, water and solvent overhead. Typical stripper column pressures are from about atmospheric to about 100 psig., although the top of the stripper column is generally maintained at from about 1 to about 20 psig. The reboiler temperature is dependent upon the solvent and the hydrocarbon feedstock, but generally, the extractive distillation column bottom temperature will be from about 135° to about 180° C.

Figure 2:
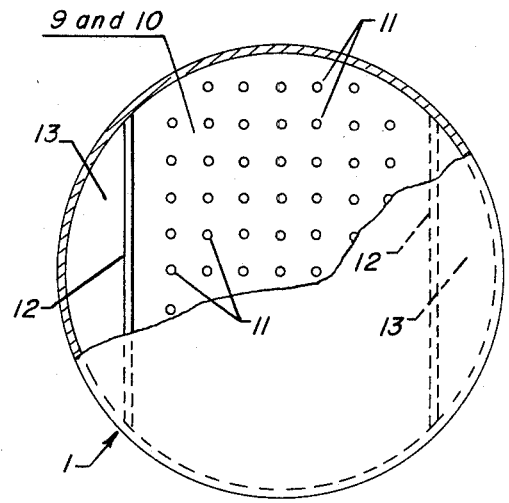

The attached drawings, FIGS. 1 and 2, illustrate one preferred embodiment of the multiple stage extractor column of the subject invention. In the drawings, corresponding parts have corresponding numbers. There is shown a multiple stage extractor column (FIG. 1) comprising an elongated vertical shell 1 having an overhead raffinate outlet means 2, an upper lean solvent inlet means 3, an intermediate hydrocarbon feedstock inlet means 4, a lower hydrocarbon reflux inlet means 5, and a bottom rich solvent outlet means 6. The vertical shell 1 encloses an upper extraction section 7 extending upwardly from the intermediate hydrocarbon feedstock inlet means 4, and a lower backwash section 8 extending downwardly from said intermediate inlet means. A first plurality of vertically spaced apart perforated extraction trays 9 are contained in the upper extraction section 7, and the lower backwash section 8 contains a second plurality of trays 10.

Each of the several extraction trays (FIG. 2) is characterized by a number of perforations 11 having substantially the same cross-sectional area and uniformly distributed across the contacting surface thereof. Each of said trays is further characterized by a chordal shaped opening and by a weir 12 attached to the chordal periphery of said tray to form a conduit 13 for transferring the hydrocarbon phase upwardly between the several stages, said conduit being commonly referred to as a riser or upcomer means. While the cross-sectional area of the upcomer 13 is shown a chordal shaped, the upcomer may have a circular shaped cross-sectional area, or any other suitably shaped cross-sectional area. In the drawing, representing one preferred embodiment of the invention, the extraction trays of the backwash section are shown vertically spaced apart at a distance which is about half again greater than the spacing between the trays of the upper extraction section.

In operation, a lean solvent is introduced into the extractor column by way of line 16 and enters the uppermost stage of the extraction section 7. The solvent phase then gravitates downwardly through the multiple stage extractor column passing through said first plurality of extraction trays, and then through said second plurality of extraction trays, each of said trays being adapted to accumulate a layer of solvent thereon while dispersing the same as droplets through the stage below. The mixed hydrocarbon feedstock, containing some $C_9$ aromatics, is introduced into the extractor column through line 15 and moves upwardly in countercurrent stagewise contact with the denser gravitating solvent. The hydrocarbon phase passes as a continuous stream into each stage above the solvent layer contained therein and then across the stage into the upcomer 13 and into the next higher stage, said hydrocarbon phase being contacted while passing laterally across each stage by solvent droplets raining down through each stage from the perforated tray above. A resulting raffinate stream, comprising substantially all of the higher molecular weight non-aromatic hydrocarbons, is withdrawn through an overhead line 14 and further treated in accordance with prior art practice.

A light hydrocarbon backwash stream is introduced into the backwash section 8 by way of line 17. The backwash stream is the overhead product from an extraction stripper column heretofore described but not shown in the drawing. In addition to light non-aromatic hydrocarbons, the backwash stream will contain some light aromatics, principally benzene, as is typically the case. The light hydrocarbon backwash stream serves to strip the heavier non-aromatics from the aromatic-rich solvent moving downwardly from the extraction section 7 of the extractor column. The heavier non-aromatics re-enter the hydrocarbon phase to be recovered in the overhead raffinate stream. In addition, the lighter aromatics in the hydrocarbon backwash stream displace the heavier $C_9$ aromatics from the aromatic-rich solvent, and the displaced $C_9$ aromatics also re-enter the hydrocarbon phase. However, while the heavier non-aromatic hydrocarbons are recovered in the overhead raffinate stream, the $C_9$ aromatic hydrocarbons are re-dissolved in the lean solvent stream in the upper stages of the extraction section 7, and, as heretofore mentioned, this cycle continues to build until the $C_9$ aromatics escaping through line 18 with the aromatic-rich solvent substantially equals the $C_9$ aromatics in the hydrocarbon feedstock. In the practice of this invention, the velocity of the hydrocarbon phase horizontally traversing the various stages of the backwash section is moderated by reason of the increased spacing between trays, and the tendency of the solvent droplets to be swept up through the upcomer means is substantially obviated. As a consequence, the solvent/hydrocarbon interface at the bottom of the extractor column is more readily controlled.

The prior art also includes U.S. Pat. No. 4,039,389 which discloses a liquid-liquid extraction apparatus suitable for the solvent extraction of aromatic hydrocarbons from a hydrocarbon mixture. The apparatus includes a first plurality of extraction trays in an upper portion of an extractor column having a number of uniform perforations of preselected cross-sectional area, and a second plurality of extraction trays in a lower portion of said column having a greater number of uniform perforations of said preselected cross-sectional area, each of said trays being provided with a downcomer. The apparatus is designed to provide high efficiency in extraction operations over a wide range of flow rates. However, the apparatus does not provide a backwash section as herein contemplated, nor would the tray design and arrangement afford a solution to the problem to which the present invention is addressed.

I claim as my invention:

1. A multiple stage extractor column for countercurrent contact of an upwardly moving hydrocarbon phase and a downwardly moving solvent phase which comprises:

(a) an enclosed vertically elongated shell having an overhead raffinate outlet means, an upper lean solvent inlet means, an intermediate hydrocarbon feedstock inlet means, a lower hydrocarbon reflux inlet means, and a bottom aromatics-rich solvent outlet means;

(b) an upper extraction section comprising a first plurality of vertically spaced-apart perforated fixed extraction trays, including upcomer means, traversing the interior of said shell in a horizontal plane;

(c) a lower backwash section comprising a second plurality of vertically spaced-apart perforated fixed extraction trays, including upcomer means, traversing the interior of said shell in a horizontal plane wherein said upper and lower sections are divided by a line parallel to said hydrocarbon feedstock inlet means;

(d) the fixed extraction trays of said second plurality being vertically spaced from each other at a distance of from about $\frac{1}{8}$ to about $\frac{1}{2}$ greater than the distance separating the fixed extraction trays of said first plurality.

2. The extractor column of claim 1 further characterized in that the spacing between said first plurality of extraction trays is from about 0.5' to about 1.5'.

3. The extractor column of claim 1 further characterized in that said extraction trays comprise perforations of substantially uniform cross-sectional are uniformly distributed across the contacting area thereof.

4. The extractor column of claim 1 further characterized in that the upcomer means associated with each of said extraction trays have a substantially uniform cross-sectional area.

* * * * *